United States Patent
Sørensen et al.

(10) Patent No.: US 11,109,751 B2
(45) Date of Patent: Sep. 7, 2021

(54) ILLUMINATION SYSTEM FOR AN ENDOSCOPE

(71) Applicant: Ambu A/S, Ballerup (DK)

(72) Inventors: Morten Sørensen, Ballerup (DK); Thomas Bachgaard Jensen, Copenhagen (DK)

(73) Assignee: AMBU A/S, Ballerup (DK)

(*) Notice: Subject to any disclaimer, the term of this patent is extended or adjusted under 35 U.S.C. 154(b) by 403 days.

(21) Appl. No.: 16/212,865

(22) Filed: Dec. 7, 2018

(65) Prior Publication Data

US 2019/0175007 A1 Jun. 13, 2019

(30) Foreign Application Priority Data

Dec. 8, 2017 (EP) .................................. 17206235

(51) Int. Cl.
| | |
|---|---|
| *A61B 1/00* | (2006.01) |
| *A61B 1/07* | (2006.01) |
| *G02B 23/24* | (2006.01) |
| *A61B 1/05* | (2006.01) |

(Continued)

(52) U.S. Cl.
CPC .............. *A61B 1/07* (2013.01); *A61B 1/0011* (2013.01); *A61B 1/00096* (2013.01); *A61B 1/00117* (2013.01); *A61B 1/00126* (2013.01); *A61B 1/05* (2013.01); *A61B 1/0669* (2013.01); *G02B 23/2461* (2013.01); *A61B 1/0017* (2013.01); *A61B 1/00167* (2013.01); *G02B 6/0006* (2013.01)

(58) Field of Classification Search
None
See application file for complete search history.

(56) References Cited

U.S. PATENT DOCUMENTS

| | | | | |
|---|---|---|---|---|
| 4,272,156 A | * | 6/1981 | Ishibashi ............ | A61B 1/00117 385/117 |
| 6,219,480 B1 | * | 4/2001 | Cassarly .............. | G02B 6/2804 385/31 |
| 8,790,250 B2 | | 7/2014 | Petersen et al. | |

(Continued)

FOREIGN PATENT DOCUMENTS

| | | |
|---|---|---|
| DE | 102013226019 | 6/2015 |
| JP | S59-182407 A | 10/1984 |

(Continued)

OTHER PUBLICATIONS

English Translation of JPH 07-246189.*
Search Report Issued in EP 17206235.8 dated Jun. 6, 2018, 4 pages.

*Primary Examiner* — Timothy J Neal
(74) *Attorney, Agent, or Firm* — Faegre Drinker Biddle & Reath LLP

(57) ABSTRACT

An endoscope includes a hollow handle housing and an insertion tube including a tip part at the distal end of the endoscope. The tip part includes an illumination arrangement with an elongated single-piece light guide having a proximal light guide end and at least one distal light guide end, wherein the proximal light guide end is adapted for receiving at least one light fiber. The at least one distal light guide end has an end surface adapted for emitting the light from a light source. The cross-section of the proximal light guide end differs from the cross-section of the at least another part of the light guide.

22 Claims, 4 Drawing Sheets

(51) Int. Cl.
*A61B 1/06* (2006.01)
*F21V 8/00* (2006.01)

(56) References Cited

U.S. PATENT DOCUMENTS

| | | | |
|---|---|---|---|
| 9,220,400 B2 | 12/2015 | Petersen | |
| 9,526,425 B2 | 12/2016 | Feldman et al. | |
| 9,572,482 B2 | 2/2017 | Lin | |
| 9,968,241 B2 | 5/2018 | Iuel | |
| 10,149,602 B2 | 12/2018 | Daher et al. | |
| 10,149,605 B2 | 12/2018 | Petersen et al. | |
| 2007/0019916 A1* | 1/2007 | Takami | A61B 1/00167 385/117 |
| 2009/0203966 A1* | 8/2009 | Mizuyoshi | G02B 23/26 600/182 |
| 2011/0288372 A1 | 11/2011 | Petersen | |
| 2011/0306831 A1 | 12/2011 | Kohnke Ole | |
| 2012/0271115 A1 | 10/2012 | Buerk | |
| 2013/0223802 A1 | 8/2013 | Dahmen | |
| 2014/0347878 A1* | 11/2014 | Honda | A61B 1/00177 362/574 |
| 2015/0282701 A1* | 10/2015 | Oskin | A61B 1/00066 600/131 |
| 2015/0335227 A1 | 11/2015 | Jacobsen et al. | |
| 2017/0035282 A1 | 2/2017 | Kaneko | |
| 2018/0296069 A1 | 10/2018 | Matthison-Hansen | |
| 2018/0303315 A1 | 10/2018 | Matthison-Hansen | |
| 2018/0303317 A1 | 10/2018 | Matthison-Hansen | |
| 2018/0303472 A1 | 10/2018 | Matthison-Hansen et al. | |
| 2018/0309908 A1 | 10/2018 | Matthison-Hansen et al. | |

FOREIGN PATENT DOCUMENTS

| | | | | |
|---|---|---|---|---|
| JP | H 07-246189 | * | 9/1995 | A61B 1/00 |
| WO | 2014106511 | | 7/2014 | |
| WO | 2016/005154 A1 | | 1/2016 | |

* cited by examiner

ILLUMINATION SYSTEM FOR AN ENDOSCOPE

CROSS-REFERENCE TO RELATED APPLICATIONS

This application claims priority under 35 U.S.C. § 119(b) from European Application No. 17206235, filed on Dec. 8, 2017, which is expressly incorporated herein by reference in its entirety.

TECHNICAL FIELD

The present invention relates to an illumination system for an endoscope, more specifically to an endoscope comprising an insertion tube with a tip part comprising an illumination arrangement adapted for emitting light emanating from a light source.

BACKGROUND OF THE DISCLOSURE

As the name indicates, endoscopes are used for seeing inside things, such as lungs or other human body cavities of a patient. Modern endoscopes are therefore typically equipped with a least one camera or similar image capturing device at the distal tip of the endoscope. Provided that sufficient light is present, this allows the operator to see where the endoscope is steered and to set the target of interest once the tip has been advanced thereto. This therefore normally requires illumination of the area in front of the distal tip of the endoscope, in particular the field of vision of the camera(s). One known way of achieving such illumination is to provide Light Emitting Diodes (LEDs) in the tip of the endoscope, as e.g. mentioned in WO2014/106511 disclosing a disposable endoscope.

Though providing LEDs in the tip of the endoscope is in many ways efficient and has largely proved itself a success, there are however some minor drawbacks that speak against this approach to illumination. One is that the LEDs themselves take up space in the tip part, where space is sparse. Furthermore, the LEDs and any associated electronics dissipate heat, which puts strict restrictions on the amount of light which can be produced by LEDs in the tip part itself, when the endoscope is inserted into a patient. Also, the LEDs need an electrical supply, meaning that electrical supply wires need to be drawn at least from the handle through the insertion tube, including the bending section thereof, and into the tip part forming, in WO2014/106511, the most distal segment of the bending section. Since LEDs are more or less point light sources, providing a desired light distribution in front of the tip part is therefore difficult, and may need a number of LEDs. A good and well defined light distribution is desired, because illuminating parts of minor interest less than parts of high interest will lead to underexposure of the image capture device for the parts of high interest, thereby making them invisible to the image capture device and in turn the operator relying on the image.

Another known way of providing illumination is to use an optical fiber to transmit light from a remote light source to the distal tip of the endoscope where it is emitted. DE10 2013 226 019 discloses one such solution. DE10 2013 226 019 suggests that the remote light source may be located within the endoscope itself or externally thereof and light be directed to the distal end via multiple fibers. DE10 2013 226 019 specifically deals with the emission of light in multiple directions i.e. angles different from 0° with respect to the longitudinal direction of the insertion tube, and accordingly uses multiple fibers. In one embodiment it is suggested to use a Fused Fibre Element (FFE) as a small light diverting element at the distal end of the endoscope. The arrangements of DE10 2013 226 019 are not only quite specific, but also utilizes a large number of different and complicated components such as the FFEs, which do not render themselves for implementation in a disposable endoscope such as the one disclosed in WO2014/106511.

On this background it is the object of the present invention to provide an endoscope with a new and improved illumination arrangement.

SUMMARY OF DISCLOSED EMBODIMENTS

The present invention relates to an illumination system for an endoscope and to an endoscope including said illumination system. In some embodiments, the endoscope comprises a handle comprising a hollow handle housing and an insertion tube extending from the handle towards a distal end of the endoscope, where the insertion tube comprises a tip part comprising an illumination arrangement adapted for emitting light emanating from a light source.

According to a first aspect of the invention, this object is achieved by an endoscope comprising a handle comprising a hollow handle housing and an insertion tube extending from the handle towards a distal end of the endoscope, where the insertion tube comprises a tip part at the distal end of the endoscope, said tip part comprising an illumination arrangement adapted for emitting light emanating from a light source, where said illumination arrangement comprises an elongated single-piece light guide having a proximal light guide end and at least one distal light guide end, where the proximal light guide end is adapted for receiving at least one light fiber and the at least one distal light guide end is adapted for emitting the light from the light source, wherein the cross-section of the proximal light guide end differs from the cross-section of at least one other part of the light guide, preferably the cross-section at the distal light guide end.

By the use of such an elongated single-piece light guide in the illumination arrangement in the tip part, it becomes possible to provide a desired light distribution in front of the tip part, while at the same time overcoming one or more of the other prior art drawbacks mentioned above. Furthermore, the use of a light fiber to conduct the light to the light guide reduces the number of electrical wires to be drawn from the handle to the tip part. Also, using a single-piece light guide allows manufacture of the single-piece from a rigid material, as compared to the non-rigid light fiber, in turn making the handling in manufacture and assembly easier.

According to one embodiment, the light guide comprises one or more prongs. A light guide comprising one or more prongs may have several distal light guide ends. By the use of a light guide comprising two or more distal light guide ends and by the light guide bending the light inside the light guide towards the distal light guide ends, lighting may be provided in front of the tip part from multiple angles. It is thereby possible to achieve additional lighting profiles leading to an improved illumination in front of the tip. It is also possible to ensure good illumination while taking into account the space occupied by other parts of the tip of the endoscope such as the working channel, camera, electronics etc.

According to another preferred embodiment, the at least one distal light guide end surface comprises a circular light guide end surface. Using a circular light guide end surface allows good control of the emission directions of the light out of the light guide.

According to yet another preferred embodiment, the light guide comprises two prongs, each prong having a semi-circular light guide end surface. This allows the prongs to have together essentially the same shape and cross-sectional area as the rest of the light guide, in turn, reduces light losses, as compared to embodiments where the cross-section changes in shape and/or area.

According to a further preferred embodiment, at least a portion of the edges of the at least one distal light guide end is chamfered or outwards angled around the light guide end surface. This further provides a good control over the emission directions of the light out of the light guide.

According to yet a further preferred embodiment, the light guide is solid. This allows the light guide to be manufactured in one single integral piece. This in turn is cost efficient, but at the same time allows good control of the optical properties of the light guide.

According to yet another preferred embodiment, at least a portion of said at least one light fiber is cladded. This gives good protection for the light fiber along the length of the insertion tube of the endoscope towards the light guide at the distal end thereof. Moreover, it makes it possible to exert some control over where the light fiber touches other parts of the endoscope, in order to maintain high internal reflection within the fiber. The same applies to the light guide when, according to a further preferred embodiment, at least a portion of said light guide is cladded.

According to a further preferred embodiment, the at least one light fiber comprises a proximal light fiber end and a distal light fiber end, said light guide being adapted to surround said distal light fiber end. This allows good contact, optical connection and coupling of light between the distal end of the light fiber and the light guide. This will even be the case when, according to a further embodiment, at least one light fiber and said proximal light guide end are connected to each other using an adhesive. With a suitable transparent adhesive, the optical connection and coupling of light between the distal end of the light fiber and the light guide may even be better than without any adhesive.

According to another embodiment the proximal end of the light guide has the same cross-sectional shape and area as the light fiber. Preferably, a section of the light guide at the proximal end has a cylindrical shape with a diameter equivalent to, or even the same, as the diameter of the light fiber. This has the advantage that light is transferred from the light fiber to the light guide without any considerable change in the angle at which the light rays are incident to and reflected from the sidewall of the light guide. This minimizes the risk that a fraction of the light rays is not reflected but transferred through the light guide wall, and thereby lost.

According to another preferred embodiment, the light guide at least partially surrounds an electronics assembly. In this way the light guide may also serve as a part of a protective housing for the electronics.

According to yet another preferred embodiment, the endoscope comprising an optical lens adapted to transmit light emanating from the at least one distal light guide end. Such a lens may provide the dual functions of protecting the distal light guide end, as well as further controlling the direction and distribution of the light.

According to a specifically preferred embodiment, the endoscope comprises a light source connected to the handle. Having the light source outside the handle, rather than inside, allows the light source to be placed at a location where excess heat from the light source may efficiently be dissipated. Accordingly, as compared to a location within the handle or even in the tip of the endoscope a more powerful light source producing more waste heat may be utilized without any discomfort to the operator or the patient. Furthermore, more space will be available allowing for other types of light sources as compared to the prior art in which LED's are currently used in the tip part. Furthermore, having the light source in a non-disposable part, allows the light source and at least some of the associated electronics to be reused, reduces the amount of electronics in the waste to be handled.

BRIEF DESCRIPTION OF THE DRAWINGS

The invention will now be described in based on nonlimiting exemplary embodiments and with reference to the drawings, on which.

DETAILED DESCRIPTION

Figure 1:
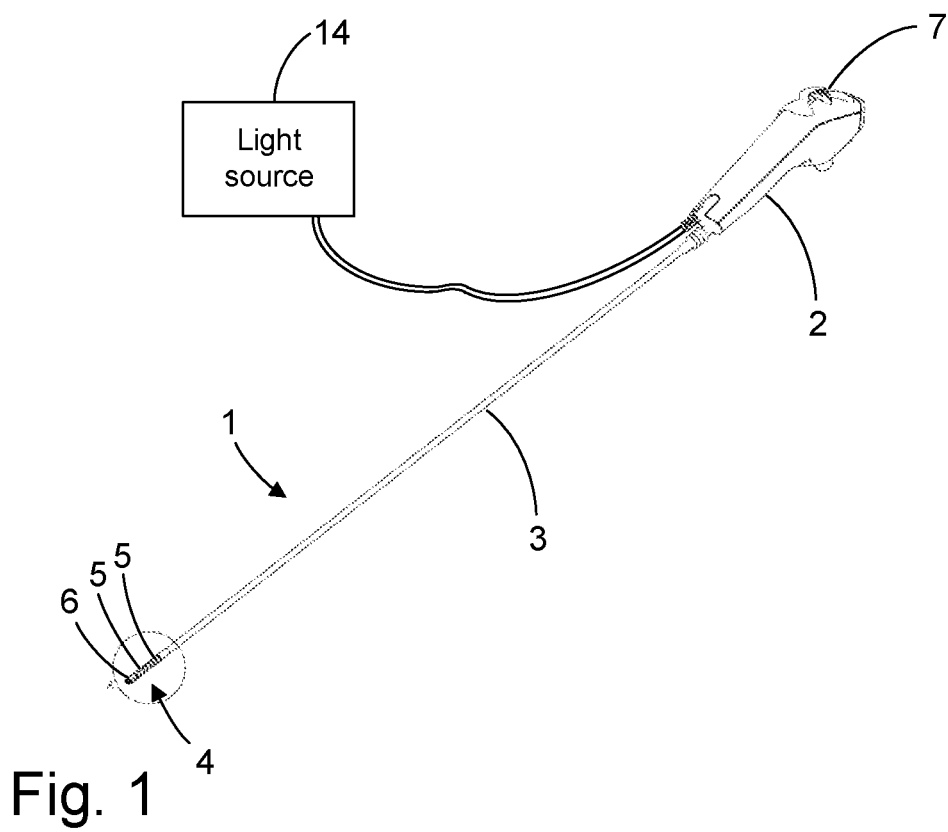
FIG. 1 shows an endoscope according to one embodiment of the invention and comprising external light source.

FIG. 1 generally shows an endoscope 1. The endoscope 1 has a handle 2 forming the proximal end of the endoscope 1. From the handle 2 an insertion tube 3 extends. The insertion tube 3 terminates in a bending section 4 forming the distal end of the endoscope 1. The bending section 4 comprises a number of hinged or otherwise articulated segments 5, 6 allowing it to bend under the control of an operator using a control lever 7 at the handle 2. The most distal segment 6 forms the distal tip of the endoscope 1 as well as of the insertion tube 2. These general details of an endoscope are per se well known, e.g. from the aforementioned WO2014/106511 incorporated herein by reference.

Figure 2:
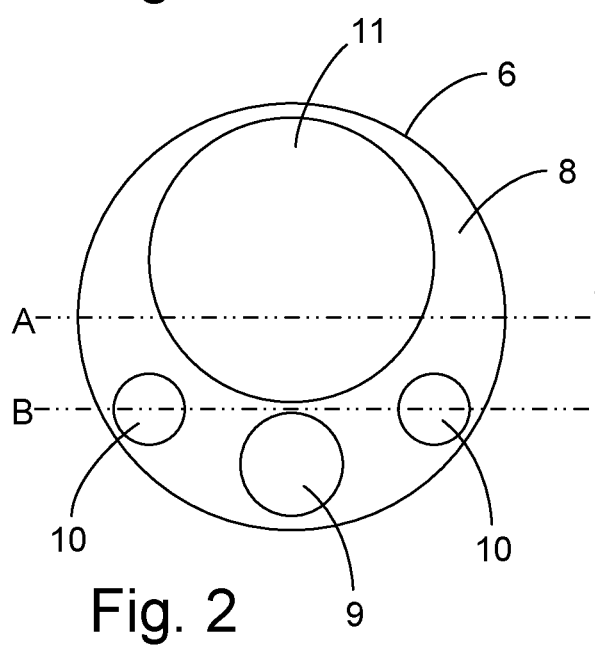
FIG. 2 shows an end view of the distal tip of the endoscope according to a first embodiment of the invention.
Figure 3:
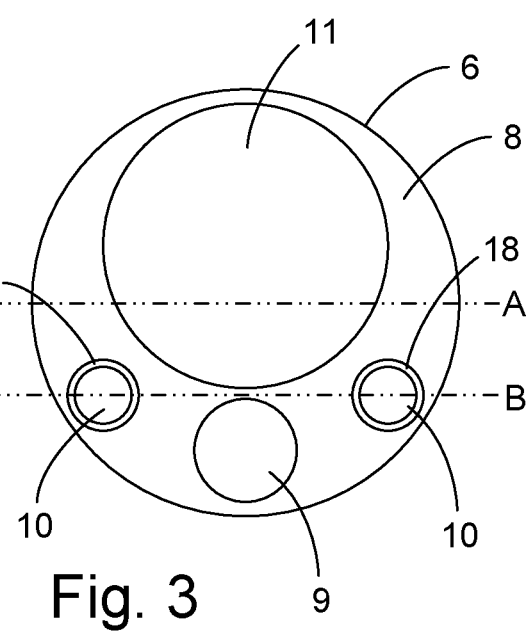
FIG. 3 shows an end view of the distal tip of the endoscope according to a second embodiment of the invention.

FIGS. 2 and 3 show the end face 8 of the most distal segment 6 of the bending section 4. The end face 8 comprises an aperture for an image capture device 9, which is preferably a camera, but other image sensors or even fiber optics are not excluded. For the image capture device 9 to function light is required. Light is therefore provided by one or more illumination devices 10. The most distal segment 6 also includes a port functioning as an inlet or outlet of a working channel 11 and/or a suction extending through the insertion tube 3 to the handle 2 where a further port (not shown) is located.

Figure 4:
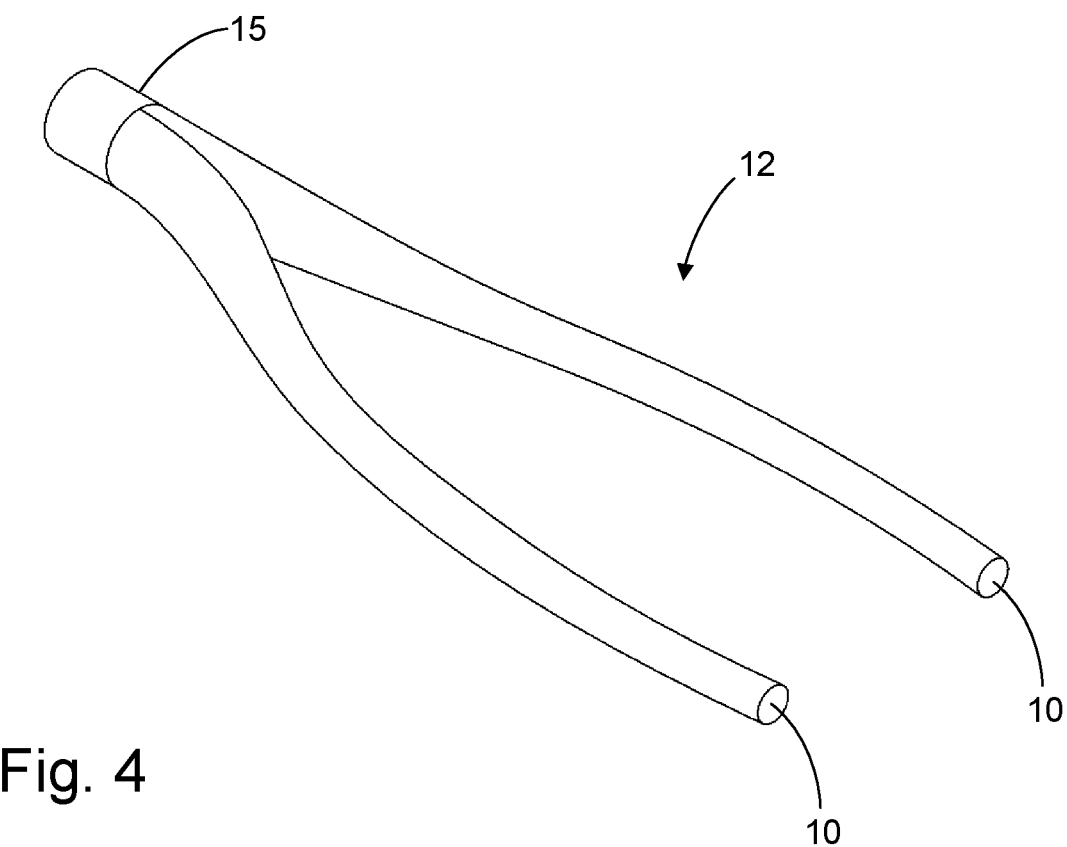
FIG. 4 shows a light guide according to the invention.
Figure 5:
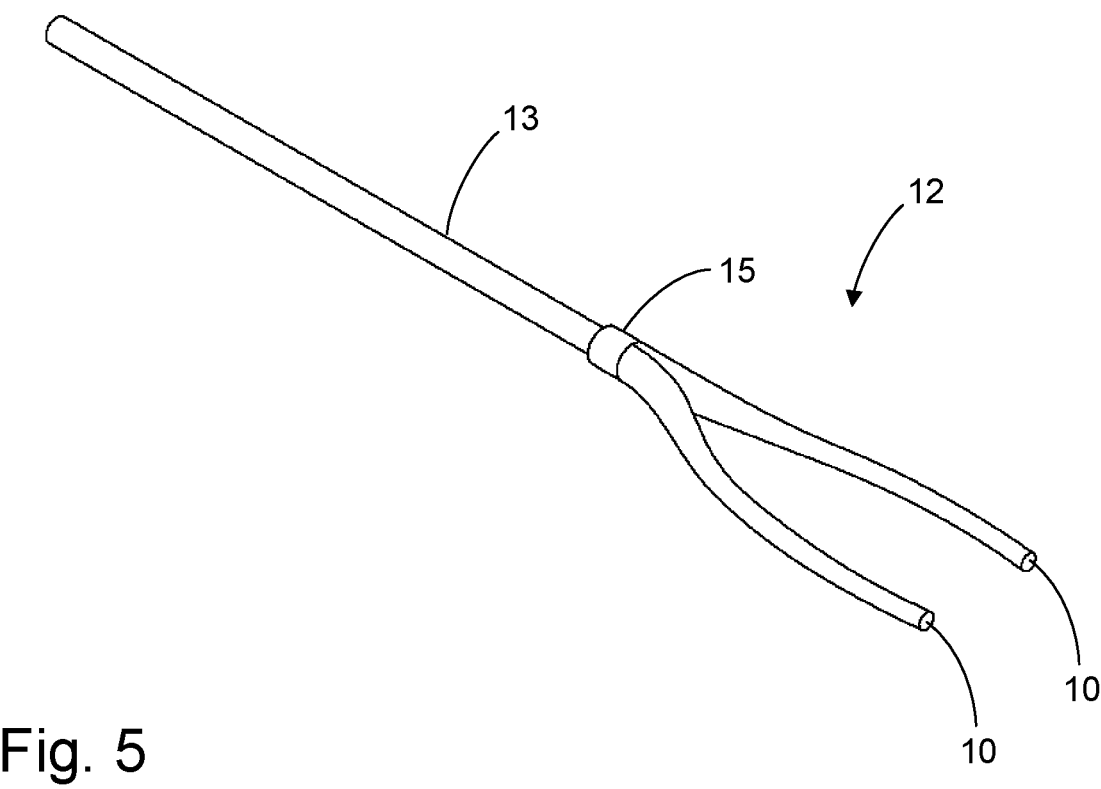
FIG. 5 shows the light guide of FIG. 4 connected to a light fiber.

According to the present invention the one or more illumination devices 10 comprise a light guide 12 of which a preferred embodiment is shown in FIG. 4. The light guide 12 is connected to a light fiber 13, preferably one single light fiber 13 only, in particular one single single-core fiber only. Light from a remote light source 14, i.e. away from the most distal segment 6 is fed into the light fiber from that remote location in a manner well known and conventional for the skilled person. The remote location could be an external light source 14 connected to the endoscope via a cable comprising the light fiber 13, or it could be a light source integrated in the body of the endoscope 1 itself, e.g. in the handle 2. Having an external light source 14 connected to the endoscope 1 solves heating problems, as the heat produced by powerful light sources such as xenon-bulbs, banks of LEDs, or other light bulbs may readily be dissipated without the risk of heating the handle 2 of the endoscope 1 to the discomfort of the operator, or without causing a considerable constraint on the obtainable amount of light, by having the LED in the in the most distal segment 6. If the light source is located within the handle 2 of the endoscope 1, a single LED is currently preferred for easy coupling of the light.

Figure 6:
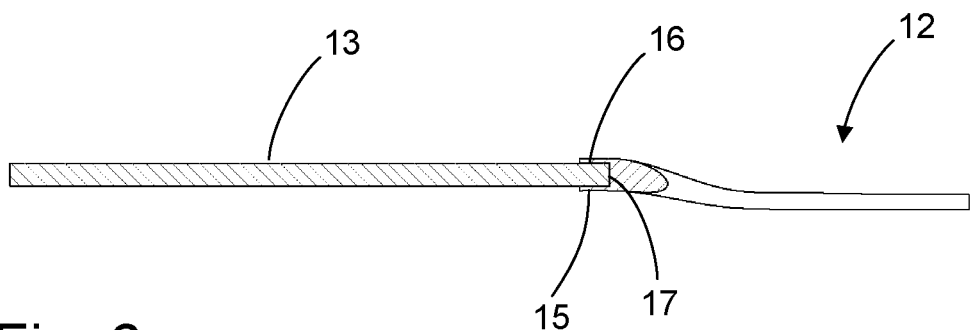
FIG. 6 shows a cross-section of the light guide and light fiber of FIG. 5.
Figure 7:
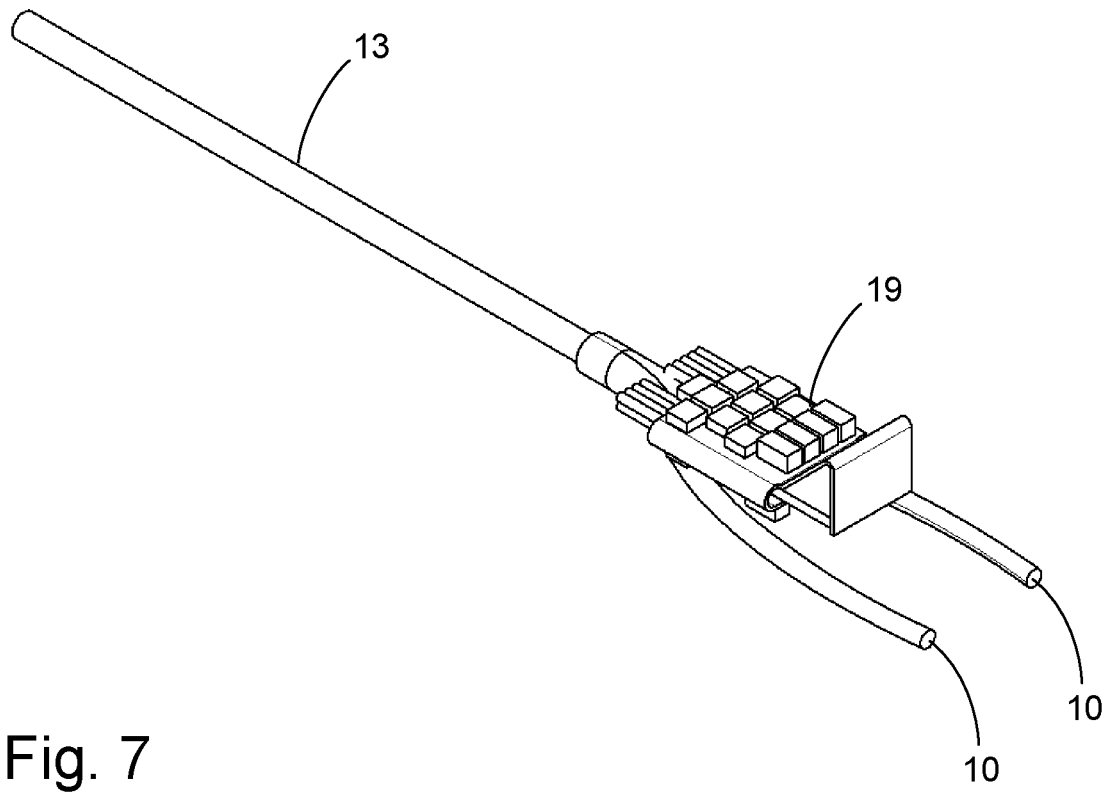
FIG. 7 shows the light guide and light fiber of FIG. 5 in conjunction with an electronics module

Preferably, the light guide 12 is embedded in the most distal segment 6 only. Unlike the light fiber 13 it can therefore be made rigid, as it does not need to bend. The light guide can therefore be made as a single piece of rigid material with the suitable optical properties, e.g. by injection molding or similar economically beneficial manufacturing process. Among the numerous suitable materials, Polycarbonate, PMMA, COC and COP are preferred. Having the light guide as a relatively rigid single-piece object also facilitates the handling during manufacturing and assembly, such as placement in the tip part. The proximal end 15 of the light guide is preferably cylindrical with a central axial bore 16 for accommodating the distal end 17 of the light fiber 13 as can best be seen in FIG. 6. Inserting the distal end 17 in such a bore 16 ensures that all light emanating from the distal end 17 of the light fiber 13 is coupled into the light guide 12. Light fibers 13 normally have a circular cross-section, and the internal diameter of the bore 16 is therefore preferably adapted to match the external diameter of the light fiber 13. To secure the distal end 17 of the light fiber in the bore 16 a suitable adhesive is preferably applied. A suitable adhesive would of course exhibit the necessary mechanical properties, but also be transparent with a suitable index of refraction (i.e. as close as possible to the index of refraction of both the light fiber and the light guide materials) to avoid reflections in light transmitting interfaces between the light fiber 13 and the light guide 12. On the other hand, the bottom of the bore 16 could have a curvature and the index of refraction of the glue and/or the light fiber could be suitably chosen to provide an optical lens property.

From the cylindrical proximal end 15 the light guide changes its cross-section. The cross-section may change in shape as well as in area, and preferably in both. Thus, from the cylindrical proximal end the circular cross-section part of light guide 12, the geometry of the cross-sectional area diverts into two prongs which not only have different cross-sectional areas but evidently also a shape differing from the single circular cross-section, i.e. two circular cross-sections. This allows the light to be guided to a suitable location from which it is to be emitted. More specifically, as can be seen from FIGS. 2 and 3 the centers of the two cross-sections at the distal light guide ends 10 lie in a common plane B which has an off-set from a center plane A of the most distal tip segment 6. The center plane A coincides with the plane in which the hinges or articulations between the segments 5, 6 lie, when the bending section 4 is straight. Since, at least along the segments 5, the light fiber 13 needs to be able to bend too, it is advantageous that the light fiber 13 is a single light fiber and that it also lies in this center plane A. Consequently, the light guide 12 also serves the purpose of directing the light away from this center plane A to a location where it is desired to emit the light. Using a single bendable light fiber 13 also makes it easier to incorporate in the remainder of the endoscope 1, such as the insertion tube 3.

The one or more distal end faces 10 of the light guide are preferably plane and perpendicular to the center plane A to ensure that light is primarily emitted in a direction in front of the distal tip part into the field of vision of the image capture device 8. However, it is not excluded that they may instead have a curvature to provide optical lens properties to emit the light in a desirable way, or be plane at an angle to the center plane A to emit light in a de-sired direction. It is furthermore also not excluded that an additional optical lens or lens system is provided in front of the one or more distal end faces 10 of the light guide 12 to provide e.g. a collimation profile, converging profile, dispersion profile or a specific light emission profile.

Figure 9:
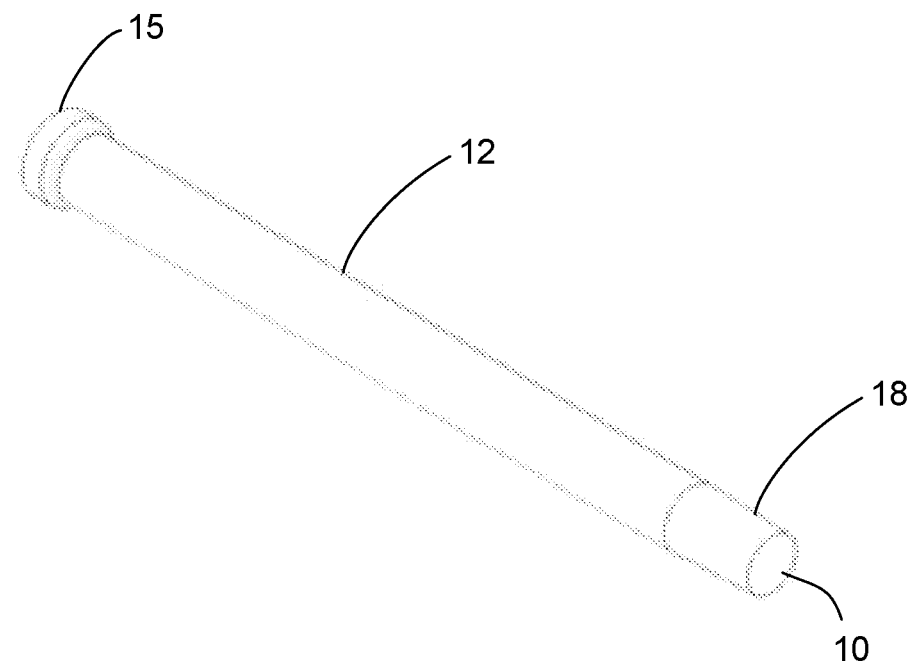
FIG. 9 shows a further embodiment of the invention with a tapering conical part.
Figure 10:
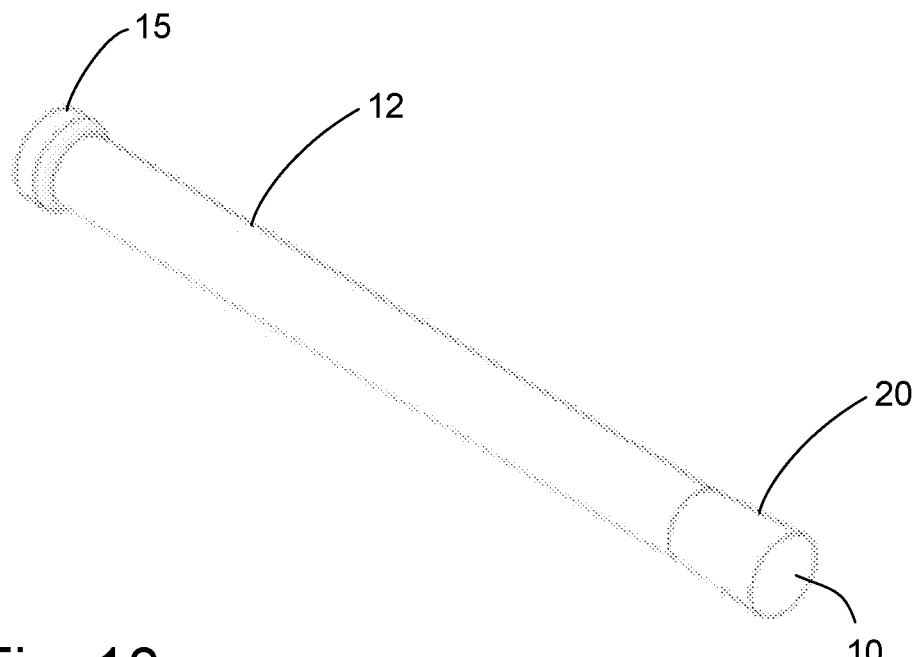
FIG. 10 shows a further embodiment of the invention with an expanding conical part.

Furthermore, the edges of the distal end face 10 of the light guide 12 may have a chamfer 18, thereby reducing the cross-sectional area as illustrated in FIGS. 3 and 9, so as to obtain a specific collimation profile of the light emitted from the distal end of the light guide 12. This collimation profile will depend on the angle and length of the chamfer 18, and the angle as such is mainly a matter of choice for the skilled person. Alternatively, as illustrated in FIG. 10 the cross-sectional area may be increased at the distal tip towards the distal end face 10, e.g. having flared or frustro-conical section 20. With a suitable choice of features such as chamfer 18, curvature of the end surface, shape of the end surface, number of end surfaces it will, in particular, be possible to increase the intensity in the middle of the light emission profile, i.e. the center of the image captured by the image capture device 8 and to re-duce light intensity at the sides where it may lead to over exposure of the image captured by the image capture device 8. The invention may thus in-crease the total amount of light in the image and the peak intensity of the light in the areas of interest in the image, thereby improving image quality. This is further enhanced by the fact that the external light source 14 in con-junction with the low light losses in the light fiber 13 and the light guide 12 allows a high intensity of illumination as compared to traditional LED's placed in the tip. The fact that by nature light only exits from the distal end of the light guide 12 also suppresses unwanted stray light laterally into the image capture device embedded in the most distal segment 6. As will be understood the use of a chamfer 18 is applicable to the light guide irrespective of whether there is only a single distal end face 10 as illustrated in FIG. 9 or a multiple branch distal end 10 as illustrated in FIG. 3. The same applies to the use of the flared or frustro-conical section 20 of FIG. 10 which may also be used in a multiple branch distal end 10.

The light guide is easily fitted into the most distal segment 6 together with the image capture device 8. The shape may also be chosen so that it furthermore becomes easy to place and accommodate associate parts, such as an electronics assembly 19 in the most distal segment 6. This makes it possible to reduce the outer dimension of the most distal segment 6 distal tip part of the endoscope 1. This efficient packing is further enhanced by the fact that no heat needs to be dissipated from any light source in the most distal segment 6 and therefore no compromises in packing density need to be made in order to allow for cooling a light source.

It is therefore also not a problem to embed the various components of the most distal segment 6 in suitable plastic material to protect them from the environment.

Figures 8A, 8B, 8C, 8D:
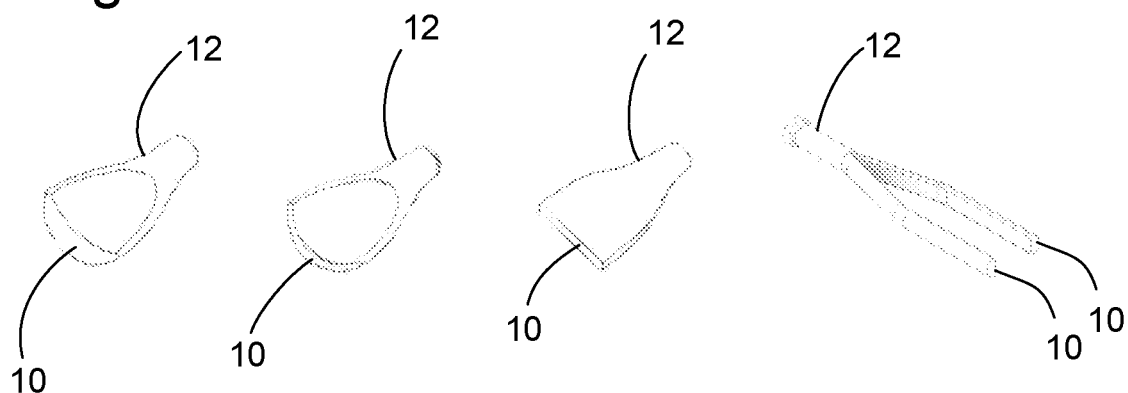
FIGS. 8a-8d show alternative embodiment of the light guide according to the invention.

Though the preferred embodiment shown use a two-pronged bifurcated light guide 12 not unlike a pitchfork, the skilled person will understand that other geometries could be used. For instance, the distal end surface 10 of the light guide 12 could comprise one or more crescents, e.g. so that the light guide 12 resembles a scoop rather than a pitchfork as illustrated in FIGS. 8*a* and 8*b* or comprise a straight or rectangle to more resemble as dustpan as in FIG. 8*c*, or annular to provide a ring shape around the image capture device 8. In those latter cases the light guide 12 can even be shaped to constitute a housing for some of the other components such as the image capture device 8 or the electronics assembly 19. Furthermore, the skilled person will understand that selected shapes may also be used for the individual end faces of two pronged or multiple pronged embodiments of the light guide 12, e.g. semi-circular as illustrated in FIG. 8*d*. In the embodiment of FIG. 8*d* the combined cross-sectional area of the end surfaces 10 are preferably the same as the remainder of the light guide 12, i.e. as if the light guide 12 was partially cleaved from the distal end towards the proximal end. That is to say splitting the cylindrical part into two parts with semi-circular cross-sections all the way to the distal end surfaces 10, while maintaining the overall cross-sectional area. This embodiment has the advantage that there is less loss of light, as compared to embodiments where the shapes of the prongs change. These are however just a few examples and the skilled person will know many more within the gist of the invention.

The single light fiber 13 is preferably a single core fiber as they are economically beneficial. The single light fiber 13 may be cladded and/or jacketed to protect the reflective properties of the light fiber 13 and/or to obtain a specific collimation profile or light emission profile of the light emitted from the distal end of the light fiber 13.

Likewise, the light guide 12 may be cladded to protect the reflective properties of the light guide 12 and/or to obtain a specific collimation or light emission profile of the light emitted from the distal end 10 of the light guide 12 based on the numerical aperture of the materials and the emission areas. This may take place in conjunction with the other measures regarding the emission and collimation profile mentioned above.

We claim:

1. An endoscope comprising:
   a handle comprising a hollow handle housing; and
   an insertion tube extending from the handle towards a distal end of the endoscope, the insertion tube having a tip part at the distal end of the endoscope, said tip part comprising an illumination arrangement adapted for emitting light emanating from a light source,
   wherein said illumination arrangement comprises an elongated single-piece light guide including a proximal light guide end having a central axial bore and a cross-section, the elongated single-piece light guide also including at least one distal light guide end having a cross-section, wherein the central axial bore of the proximal light guide end is adapted for receiving at least one light fiber and the at least one distal light guide end has an end surface adapted for emitting the light received through the central axial bore from the light source, and
   wherein the cross-section of the proximal light guide end differs from a cross-section of at least one other part of the light guide.

2. The endoscope of claim 1, wherein the at least one other part of the light guide is the distal light guide end.

3. The endoscope of claim 1, wherein the at least one distal light guide end surface comprises a circular light guide end surface.

4. The endoscope of claim 1, wherein said light guide comprises one or more prongs and has two or more distal light guide ends.

5. The endoscope of claim 1, wherein the light guide comprises two prongs, each of the two prongs having a semi-circular light guide end surface.

6. The endoscope of claim 1, wherein the at least one distal light guide end has a distal edge, and wherein at least a portion of the distal edge of the at least one distal light guide end is chamfered or outwards angled around the light guide end surface.

7. The endoscope of claim 1, wherein said at least one light fiber comprises a proximal light fiber end and a distal light fiber end, said proximal light guide end including a proximal portion being adapted to surround said distal light fiber end and a distal portion having a cross-section area and a cross-section shape that is the same as a cross-section shape and a cross-section area of the distal light fiber end.

8. The endoscope of claim 1, wherein said at least one light fiber and said proximal light guide end are connected to each other using an adhesive.

9. The endoscope of claim 1, wherein the light guide at least partially surrounds an electronics assembly.

10. The endoscope of claim 1, further comprising an optical lens arranged at the distal end of the light guide.

11. The endoscope of claim 1, further comprising a light source connected to the handle.

12. The endoscope of claim 1, further comprising a light source arranged in the hollow handle housing.

13. The endoscope of claim 1, wherein the at least one distal light guide end surface has a crescent shape.

14. The endoscope of claim 1, wherein the at least one distal light guide end surface has a generally rectangular shape.

15. The endoscope of claim 1, wherein the at least one distal light guide end has a scoop shape.

16. The illumination arrangement of claim 1, wherein the at least one distal light guide end has a chamfer comprising a decreasing cross-section area from a proximal end of the chamfer to a distal edge of the at least one distal light guide end, or the at least one distal light guide end has a flared section with an increasing cross-section area from a proximal end of the flared section to the distal edge of the at least one distal light guide end.

17. An illumination arrangement for an endoscope having a handle and an insertion tube extending from the handle, the illumination arrangement comprising:
   a single-piece light guide including a proximal light guide end and two prongs extending from the proximal light guide end, the two prongs having end surfaces at distal ends of the prongs, the proximal light guide end having a central axial bore; and
   a light fiber coupled end-to-end with the proximal light guide end and received within the central axial bore, the proximal light guide end receiving light from the light fiber through the central axial bore and the end surfaces emitting the light distally of the end surfaces, wherein a cross-section of the proximal light guide end differs from a cross-section of at least one other part of the light guide.

18. The illumination arrangement of claim 17, further comprising a distal tip, an image capture device, and an electronics assembly connected to the image capture device, wherein the light guide and at least a portion of the image capture device are positioned in the distal tip, and wherein the two prongs at least partially surround the electronics assembly.

19. The illumination arrangement of claim 17, further comprising an optical lens formed by at least one of a distal end of the light fiber, a surface of the light guide adjacent to the axial bore and facing the light fiber, or an adhesive securing the light fiber to the light guide.

20. An endoscope comprising:
a handle;
an insertion tube extending from the handle;
a single-piece light guide including a proximal light guide end and two prongs extending from the proximal light guide end, the two prongs having end surfaces at distal ends of the prongs, the proximal light guide end having a central axial bore; and
a light fiber coupled end-to-end with the proximal light guide end and received within the central axial bore, the proximal light guide end receiving light from the light fiber through the central axial bore and the end surfaces emitting the light distally of the end surfaces, wherein a cross-section of the proximal light guide end differs from a cross section of at least one other part of the light guide.

21. The endoscope of claim 20, further comprising an image capture device, an electronics assembly connected to the image capture device, and an articulation section extending from the insertion tube and including a distal tip, wherein the light guide and at least a portion of the image capture device are positioned in the distal tip.

22. The endoscope of claim 20, wherein the proximal light guide end has a distal portion and a proximal portion, the distal portion having a cross section area that is equal to a cross section area of the light fiber and the proximal portion including the central axial bore.

\* \* \* \* \*